(12) United States Patent
Kaneda et al.

(10) Patent No.: US 9,707,544 B2
(45) Date of Patent: Jul. 18, 2017

(54) SILVER-CERIUM OXIDE COMPOSITE CATALYST SUPPORTED ON AN ALKALINE CARRIER AND METHOD FOR PRODUCING THE SAME

(71) Applicants: Osaka University, Suita-shi (JP); N.E. Chemcat Corporation, Minato-ku (JP)

(72) Inventors: Kiyotomi Kaneda, Osaka (JP); Yukio Takagi, Kanagawa (JP)

(73) Assignees: OSAKA UNIVERSITY, Suita-shi (JP); N.E. CHEMCAT CORPORATION, Minato-ku (JP)

( * ) Notice: Subject to any disclaimer, the term of this patent is extended or adjusted under 35 U.S.C. 154(b) by 0 days.

(21) Appl. No.: 15/135,958

(22) Filed: Apr. 22, 2016

(65) Prior Publication Data

US 2016/0310931 A1 Oct. 27, 2016

(30) Foreign Application Priority Data

Apr. 24, 2015 (JP) ................................. 2015-089390

(51) Int. Cl.
    *C07C 1/247* (2006.01)
    *C07C 29/141* (2006.01)
    (Continued)

(52) U.S. Cl.
    CPC ............ *B01J 23/66* (2013.01); *B01J 23/007* (2013.01); *B01J 27/232* (2013.01); *B01J 35/006* (2013.01);
    (Continued)

(58) Field of Classification Search
    CPC ... B01J 21/10; B01J 23/50; B01J 23/58; B01J 23/63; B01J 23/66; B01J 37/0236; B01J 37/035; C07C 1/247; C07C 29/141
    See application file for complete search history.

(56) References Cited

U.S. PATENT DOCUMENTS

| 3,434,885 A | * | 3/1969 | Mandelkorn | ........... H01L 21/00 |
| | | | | 136/256 |
| 4,018,630 A | * | 4/1977 | Hill | ...................... H01H 1/0237 |
| | | | | 148/430 |

(Continued)

FOREIGN PATENT DOCUMENTS

| JP | 2011-236165 | 11/2011 |
| WO | WO 2014/119766 A1 | 8/2014 |

OTHER PUBLICATIONS

Lauren M. Atagi et al. "On the Mechanism of Oxygen Atom or Nitrene Group Transfer in Reactions of Epoxides and Aziridines with Tungsten (II) Compounds", J. Am. Chem. Soc., vol. 113, 1991, 5 pages.

(Continued)

*Primary Examiner* — Cam N. Nguyen
(74) *Attorney, Agent, or Firm* — Oblon, McClelland, Maier & Neustadt, L.L.P.

(57) ABSTRACT

Conventionally, a silver-cerium oxide composite containing a silver particle and cerium oxide covering the surface of the silver particle has been synthesized through a multi-stage process, and is disadvantageous not only in that there is a need to use an organic solvent and a surfactant, causing the time and cost to be increased, but also in that there is a possibility that fulminating silver is formed, leading to a problem about the safety. A method for producing a catalyst having a silver-cerium oxide composite and an alkaline carrier having supported thereon the oxide composite, the silver-cerium oxide composite containing a silver particle and cerium oxide covering the surface of the silver particle, the method having preparing a mixture containing a silver compound, a cerium compound, and an alkaline carrier, and drying the mixture is provided.

14 Claims, 3 Drawing Sheets

(51) Int. Cl.
*B01J 37/02* (2006.01)
*B01J 37/03* (2006.01)
*B01J 21/10* (2006.01)
*B01J 23/50* (2006.01)
*B01J 23/58* (2006.01)
*B01J 23/63* (2006.01)
*B01J 23/66* (2006.01)
*B01J 23/00* (2006.01)
*B01J 27/232* (2006.01)
*B01J 35/00* (2006.01)

(52) U.S. Cl.
CPC ........... *B01J 35/0086* (2013.01); *C07C 1/247* (2013.01); *C07C 29/141* (2013.01); *B01J 35/0013* (2013.01); *B01J 37/0236* (2013.01); *B01J 37/035* (2013.01); *B01J 2523/00* (2013.01); *C07C 2523/10* (2013.01); *C07C 2523/50* (2013.01); *C07C 2523/66* (2013.01)

(56) References Cited

U.S. PATENT DOCUMENTS

| | | | | |
|---|---|---|---|---|
| 5,395,812 | A * | 3/1995 | Nagase | B01J 23/66 502/238 |
| 7,030,054 | B2 * | 4/2006 | Chigapov | B01D 53/945 502/302 |
| 7,743,772 | B2 * | 6/2010 | Sundar | A24B 15/28 131/334 |
| 8,360,073 | B2 * | 1/2013 | Sundar | A24B 15/28 131/334 |
| 8,544,261 | B2 * | 10/2013 | Mori | B01D 53/944 502/304 |
| 8,637,149 | B2 * | 1/2014 | Chang | C23C 14/022 428/336 |
| 9,180,437 | B2 * | 11/2015 | Kim | B01J 23/78 |
| 2011/0311635 | A1 * | 12/2011 | Stucky | B01J 13/02 424/490 |
| 2014/0323294 | A1 * | 10/2014 | Nagao | B01J 23/34 502/304 |
| 2015/0014592 | A1 * | 1/2015 | D'Souza | B01J 21/16 252/373 |

OTHER PUBLICATIONS

T. V. Rajanbabu et al. "Selective Generation of Free Radicals from Epoxides Using a Transition-Metal Radical. A Powerful New Tool for Organic Synthesis", J. Am. Chem. Soc., vol. 116, 1994, 12 pages.

Kevin P. Gable et al. "Kinetics and Mechanism of Rhenium-Catalyzed O Atom Transfer from Epoxides", J. Am. Chem. Soc., vol. 125, 2003, 9 pages.

Kevin P. Gable et al. "Rhenium-Catalyzed Epoxide Deoxygenation: Scope and Limitations", SYNLETT, No. 14, 2003, 3 pages.

\* cited by examiner

SILVER-CERIUM OXIDE COMPOSITE CATALYST SUPPORTED ON AN ALKALINE CARRIER AND METHOD FOR PRODUCING THE SAME

FIELD OF THE INVENTION

The present invention relates to a silver-cerium oxide composite catalyst supported on an alkaline carrier and a method for producing the same.

BACKGROUND ART

A deoxygenation reaction of an epoxy compound to an alkene is a very important reaction in the fields of organic synthesis and biochemistry. With respect to the deoxygenation reaction of an epoxy compound to an alkene, the development of stoichiometric reaction using a variety of reagents has progressed (see, for example, NPL 1 and 2), but the catalytic reaction for deoxygenation has problems to be solved in that it is necessary to use a harmful reducing agent, that the reaction is likely to be affected by air or humidity, and that the catalytic activity is low (see, for example, NPL 3 and 4).

As a catalyst which enables the deoxygenation reaction of an epoxy compound to an alkene to be practically performed, for example, a silver-cerium oxide composite comprising a silver particle and cerium oxide covering the surface of the silver particle has been known. This silver-cerium oxide composite is produced by a method in which a silver solution and a cerium solution are individually changed to reversed micelle solutions, and the resultant reversed micelle solutions are mixed together to advance a redox reaction, and subsequently the micelles are caused to collapse using ethanol, and then the recovered material is calcined (see PTL 1).

However, in the above-mentioned reversed-micelle formation method, there is a problem in that the synthesis is conducted through a multi-stage process, and organic solvents and surfactants must be used, causing the time and cost to be increased. Further, there is a concern about the formation of fulminating silver which is an explosive substance. Fulminating silver is a mixture of silver nitride and silver amide, and could be generated when an aqueous ammonia solution of silver nitrate is prepared. As fulminating silver is very sensitive to an external stimulation, it is at risk of explosion caused even by slight friction, and a case in which fulminating silver actually exploded has been reported. The formation of fulminating silver can cause an accident and is a severe problem which must be avoided. Further, with respect to the reversed-micelle formation method, a method for produing a catalyst having a silver-cerium oxide composite supported on a metal oxide matrix material by a coprecipitation method has been disclosed. However, this method is likely to suffer reduction of the active surfaces due to the formation of macroparticles.

CITATION LIST

Patent Literature

PTL 1: International Publication No. WO2014/119766 pamphlet

Non Patent Literature

NPL 1: Atagi, L. M.; Over, D. E.; McAlister, D. R.; Mayer, J. M. J. Am. Chem. Soc. 1991, 113, 870

NPL 2: RajanBabu, T. V.; Nugent, W. A. J. Am. Chem. Soc. 1994, 116, 986

NPL 3: Gable, K. P.; Brown, E. C.; J. Am. Chem. Soc. 2003, 125, 11018

NPL 4: Gable, K. P.; Brown, E. C. Synlett 2003, 14, 2243

SUMMARY OF THE INVENTION

Accordingly, a task of the present invention is to provide anew form of a silver-cerium oxide composite which contains a silver particle and cerium oxide covering the surface of the silver particle, and which has excellent function as a catalyst such that it can be used in selective hydrogenation, and a method for producing the same.

The present inventors have conducted extensive and intensive studies with a view toward solving the above-mentioned problems. As a result, it has been found that, by such a simple method that includes preparing a mixture containing at least a silver compound, a cerium compound, and an alkaline carrier, and drying the mixture, a silver-cerium oxide supported composite catalyst containing a silver-cerium oxide composite formed from a nano-sized fine particle of silver-cerium oxide and an alkaline carrier having supported thereon the oxide composite can be inexpensively and safely produced, and the present invention has been completed. Further, it has been found that the thus obtained silver-cerium oxide supported composite catalyst is useful in selective hydrogenation, and the present invention has been completed.

Specifically, the invention is directed to a silver-cerium oxide supported composite catalyst containing a silver-cerium oxide composite and an alkaline carrier having supported thereon the oxide composite, wherein the silver-cerium oxide composite contains a silver particle and cerium oxide covering the surface of the silver particle.

In addition, the invention is directed to a method for producing a silver-cerium oxide supported composite catalyst which contains a silver-cerium oxide composite containing a silver particle and cerium oxide covering the surface of the silver particle and an alkaline carrier having supported thereon the oxide composite, wherein the method includes preparing a mixture containing at least a silver compound, a cerium compound, and an alkaline carrier, and drying the mixture.

Further, the invention is directed to a selective hydrogenation method for an organic compound, which includes selectively hydrogenating an organic compound using the above-mentioned silver-cerium oxide supported composite catalyst.

The silver-cerium oxide supported composite catalyst of the invention contains a silver-cerium oxide composite and an alkaline carrier having supported thereon the oxide composite, wherein the silver-cerium oxide composite contains a silver particle and cerium oxide covering the surface of the silver particle, and can be used in the applications similar to those for conventionally known silver-cerium oxide composites.

As a specific application for the silver-cerium oxide composite, for example, there can be mentioned selective hydrogenation. In the selective hydrogenation, molecular hydrogen is used as a hydrogen source, and an alcohol or carbon monoxide is not used. Thus, there is no need for an operation of separating an intended product from a by-product, which means that the use of highly toxic carbon monoxide in the hydrogenation can be avoided.

Further, the silver-cerium oxide supported composite catalyst of the invention is supported on an alkaline carrier, and therefore, after being used, the catalyst can be easily recovered by filtration. The recovered catalyst maintains the original activity and selectivity that the catalyst before use has, and therefore can be reused with ease.

The silver-cerium oxide supported composite catalyst of the invention can be produced with ease by a single-stage reaction as shown in FIG. 1. In this reaction, it is not necessary to use an organic solvent, a surfactant Igepal (registered trademark), manufactured by Rhodia Engineering Plastics, or the like, which is used in the related art as shown in FIG. 2, and water is used instead of an organic solvent. Therefore the cost can be reduced, and problems in handling an organic solvent, such as explosiveness, flammability, and toxicity, can be removed. In addition, the use of water in the production of the catalyst facilitates control of the temperature. Further, the method for producing the catalyst of the invention is safe because the formation of fulminating silver can be avoided. Furthermore, merely by checking whether the color of the precipitate in the mixture after being stirred is changed or not, it is possible to know whether the catalyst of the invention has been produced, and the judgement can be easily made.

DESCRIPTION OF THE PREFERRED EMBODIMENTS

Figure 1:
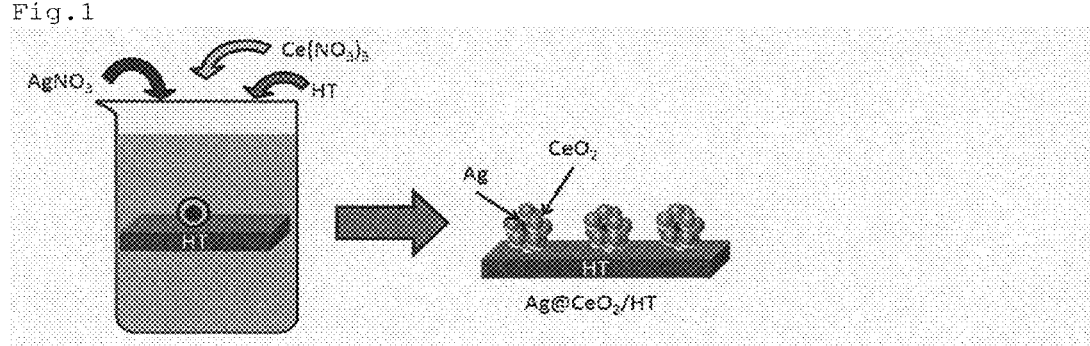
FIG. 1 is a diagrammatic view showing an example of the production of the silver-cerium oxide composite catalyst of the invention.
Figure 2:
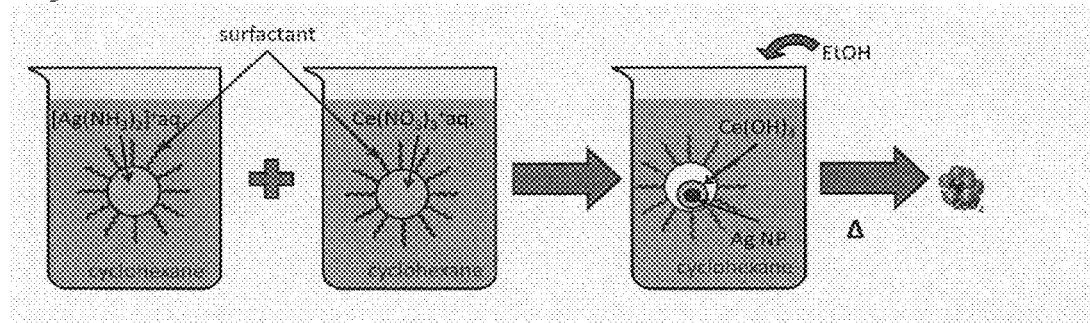
FIG. 2 is a diagrammatic view showing an example of the production of a conventional silver-cerium oxide composite catalyst.

The silver-cerium oxide supported composite catalyst of the present invention (hereinafter, referred to as "the catalyst of the invention") contains a silver-cerium oxide composite and an alkaline carrier having supported thereon the oxide composite, wherein the silver-cerium oxide composite contains a silver particle and cerium oxide covering the surface of the silver particle. Hereinbelow, the silver-cerium oxide composite and alkaline carrier constituting the catalyst of the invention will be described.

The above-mentioned silver-cerium oxide composite contains a silver nano-particle (Ag nano-particle) and/or a silver oxide nano-particle as a nucleus (core) and cerium oxide (mainly $CeO_2$, and additionally $Ce_2O_3$ or the like) covering the surface of the core, and therefore, in the present specification, the silver-cerium oxide composite is frequently represented by "AgNPs@$CeO_2$". Further, the catalyst of the invention is obtained by allowing the silver-cerium oxide composite to be supported on an alkaline carrier and consequently dispersing the silver-cerium oxide composite, and therefore the catalyst of the invention is frequently represented by "AgNPs@$CeO_2$-D".

(Silver-Cerium Oxide Composite)

The silver-cerium oxide composite, which is a catalyst component used in the catalyst of the invention, is a composite comprising a particle of a silver component (silver particle) having carried on the surface thereof a cerium oxide particle. A desirable mode of the silver-cerium oxide composite is a construction in which a silver particle constitutes a core and a cerium oxide particle is carried on the surface of the core silver particle. The silver component is at least one member of metal silver and silver oxide, and is preferably metal silver or a mixture of metal silver and silver oxide, especially preferably metal silver. The cerium oxide is at least one member of cerium dioxide ($CeO_2$) and dicerium trioxide ($Ce_2O_3$), and is preferably cerium dioxide ($CeO_2$) or a mixture of cerium dioxide ($CeO_2$) and dicerium trioxide ($Ce_2O_3$), especially preferably cerium dioxide ($CeO_2$).

In the silver-cerium oxide composite, with respect to the mode of "carrying" for the cerium oxide carried on the surface of the silver particle, there is no particular limitation. The silver-cerium oxide composite may be in various states, such as a state in which the cerium oxide is carried on and dispersed in the surface of the silver particle constituting the core so as to form an island-in-sea structure in the surface, a state in which most of the surface of the core is covered with cerium oxide but the core of the silver particle is partially exposed, and a state in which the entire surface of the core is completely covered with cerium oxide. Further, the silver-cerium oxide composite may form a cluster of the silver-cerium oxide particles, and, when the silver particles are exposed through the surface of the cluster particle, the surface of the cluster particle may be further covered with cerium oxide.

According to the above-mentioned mode of carrying, the state of the cerium oxide which is a component of the silver-cerium oxide composite can be a state of particles, a state in which the adjacent particles are connected together, a state in which the adjacent particles are further closely connected to cover the surface of the core in a network form so that the surface of the silver particle is exposed through the network, or a state in which the cerium oxide in a layer form completely covers the surface of the silver particle.

The state of the cerium oxide is also influenced by the below-mentioned Ag/$CeO_2$ molar ratio. In any case, it is desirable that the cerium oxide particles cover the silver particle to such an extent that the silver particle constituting the core can affect the substrate through the cerium oxide covering the surface of the silver particle.

With respect to the mode of the cerium oxide covering the core composed of a silver particle, there is no particular limitation as long as the silver particle constituting the core can affect the substrate through the cerium oxide covering the surface of the silver particle. For example, when the core composed of a silver particle is not completely covered with the cerium oxide but part of the core composed of a silver particle is exposed, excellent reactivity and excellent selectivity may be obtained with respect to an oxygen-containing polar functional group in the compound having a hydrogenation reactive site and the oxygen-containing polar functional group.

With respect to the cerium oxide particles covering the core composed of a silver particle which is a component of the silver-cerium oxide composite, there is no particular limitation, and the cerium oxide particles may be either primary particles or secondary particles. The cerium oxide particles preferably have an average particle diameter of 2 to 40 nm, more preferably 5 to 15 nm. In the present invention, the term "average particle diameter" means an average of the diameters of the arbitrary number of particles observed in an electron photomicrograph. When the average particle diameter (shell particle diameter) of the cerium oxide particles is 2 nm or more, the selectivity is effectively improved, and, when the average particle diameter is 40 nm or less, the activity is effectively improved.

With respect to the silver particles, there is no particular limitation as long as the particles contain silver (Ag), and the silver particles may be metal silver, or may be in an oxide state or in a composite state such that part of metal silver is in an oxide state. Specifically, the silver particles are selected from metal silver, silver oxide, and a combination thereof. Metal silver is more preferred.

The silver particles may be either primary particles or secondary particles. The silver particles preferably have an average particle diameter of 5 to 30 nm, more preferably 7 to 20 nm. In the present specification, the term "average particle diameter" means an average of the diameters of the arbitrary number of particles observed in an electron photomicrograph.

([Ag/CeO$_2$] Molar Ratio for the Silver-Cerium Oxide Composite)

In the silver-cerium oxide composite, with respect to the compositional ratio of silver in the silver particle to cerium oxide, a ratio of the mole of silver (Ag) as a metal to the mole of cerium oxide (CeO$_2$), i.e., an [Ag/CeO$_2$] molar ratio is preferably 0.25 to 4.0, more preferably 0.5 to 2.0, further preferably 0.75 to 1.0. When the [Ag/CeO$_2$] molar ratio is 0.25 or more, the conversion of an oxygen-containing polar functional group in the compound having a hydrogenation reactive site and the oxygen-containing polar functional group is effectively improved, and, when the [Ag/CeO$_2$] molar ratio is 4.0 or less, the selectivity of an oxygen-containing polar functional group in the compound having a hydrogenation reactive site and the oxygen-containing polar functional group is effectively improved.

(Particle Diameter of the Silver-Cerium Oxide Composite)

When the silver-cerium oxide composite has a shape of sphere, there is no particular limitation with respect to the particle diameter of the silver-cerium oxide composite, but the average particle diameter of the silver-cerium oxide composite is preferably 5 to 100 nm, more preferably 10 to 60 nm. When the average particle diameter of the silver-cerium oxide composite is 5 nm or more, the selectivity of an oxygen-containing polar functional group in the compound having a hydrogenation reactive site and the oxygen-containing polar functional group (hereinafter, frequently referred to as "selectivity") is effectively improved. When the average particle diameter is 100 nm or less, the conversion of an oxygen-containing polar functional group in the compound having a hydrogenation reactive site and the oxygen-containing polar functional group (hereinafter, frequently referred to as "conversion") is effectively improved.

(Core-Shell Structure of the Silver-Cerium Oxide Composite)

With respect to the structure of the silver-cerium oxide composite, there is no particular limitation, and various structures can be appropriately selected depending on the type of the substrate used in the selective hydrogenation reaction. For example, when the silver-cerium oxide composite has a so-called "core-shell structure", there is no particular limitation with respect to the size of the silver-cerium oxide composite, but the average particle diameter of the silver-cerium oxide composite is preferably 10 to 100 nm, more preferably 20 to 60 nm. When the average particle diameter of the silver-cerium oxide composite is 10 nm or more, the selectivity of an oxygen-containing polar functional group in the compound having a hydrogenation reactive site and the oxygen-containing polar functional group is effectively improved, and, when the average particle diameter is 100 nm or less, the conversion of an oxygen-containing polar functional group in the compound having a hydrogenation reactive site and the oxygen-containing polar functional group is effectively improved.

In the present invention, the term "core-shell structure" means a two-layer structure in which a shell layer composed of cerium oxide particles is formed on the surface of a core particle composed of a silver particle, and does not necessarily mean that the shell layer completely covers the core. For example, when the shell layer is composed of cerium oxide particles, the structure may be in a state in which the cerium oxide particles at least partially surround or cover the core, or in a state in which, though the surface of the core composed of a silver particle cannot be recognized using a transmission electron microscope or the like, the shell layer has a continuous gap having such a size that the substrate has access to the silver particle as the core, and the core particle composed of the silver particle is in communication with the outside of the shell layer through the gap. Further, the structure is preferably an independent particle.

Further, the state in which "the shell layer has a continuous gap having such a size that the substrate has direct access to the silver particle as the core" indicates that the shell layer covers all over the core, but the shell layer has pores such that the substrate can undergo a reaction while being subjected to actions of both the silver particle as the core and the cerium oxide as the shell layer. Further, the silver-cerium oxide composite may form a cluster comprisig particles of the silver-cerium oxide composite, and, when the silver particles are exposed through the surface of the cluster, the surface of the cluster may be further covered with cerium oxide. The cluster may be in a form of aggregate of two or more silver-cerium oxide composite particles having a core-shell structure, or in a state in which the cerium oxide component constituting the shell covers the surface of two or more silver particles constituting the core.

The size of the pores in the shell layer can be measured by a gas adsorption method using gas, such as nitrogen, helium, or krypron, or the like, which is conducted on the silver-cerium oxide composite. With respect to the size of the pores, there is no particular limitation, and the pores may have a pore diameter such that the substrate molecule can pass through the pores. As an example of the size of the pores, the average pore diameter is preferably about 0.5 to 5.0 nm so that the substrate described in the Examples shown below can pass through the pores. When the average pore diameter is smaller than 0.5 nm, it is likely that some aromatic compounds used as the substrate cannot pass through the pores in the shell layer, so that the conversion is disadvantageously lowered. On the other hand, when the average pore diameter is larger than 5.0 nm, there is a danger that the substrate cannot satisfactorily be subjected to actions of both the silver particle as the core and the cerium oxide constituting the shell layer, so that the selectivity of an oxygen-containing polar functional group in the compound having a hydrogenation reactive site and the oxygen-containing polar functional group is disadvantageously lowered.

In the particle of the silver-cerium oxide composite having a core-shell structure, the size of the silver particle constituting the core is preferably 5 to 30 nm, more preferably 7 to 20 nm. When the particle diameter of the silver particle is 5 nm or more, the selectivity of an oxygen-containing polar functional group in the compound having a hydrogenation reactive site and the oxygen-containing polar functional group is effectively improved, and, when the particle diameter of the silver particle is 30 nm or less, the conversion of an oxygen-containing polar functional group in the compound having a hydrogenation reactive site and the oxygen-containing polar functional group is effectively improved. The cerium oxide particle constituting the shell layer covers the surrounding of the silver particle constituting the core preferably as a shell layer having a thickness of 2 to 40 nm, more preferably as a shell layer having a thickness of 5 to 15 nm. When the thickness of the shell layer is 2 nm or more, the selectivity of an oxygen-containing polar functional group in the compound having a hydrogenation reactive site and the oxygen-containing polar functional group is effectively improved, and, when the thickness of the shell layer is 40 nm or less, the conversion of an oxygen-containing polar functional group in the compound having a hydrogenation reactive site and the oxygen-containing polar functional group is effectively improved.

When the silver-cerium oxide composite in the invention has a so-called core-shell structure, the silver particle constituting the core may be completely covered with the cerium oxide particle as mentioned above, but part of the silver particle constituting the core may be exposed.

Further, when the silver-cerium oxide composite has a so-called core-shell structure and the cerium oxide constituting the shell layer is in the form of particles, the average particle diameter of the cerium oxide particles is preferably 2 to 40 nm, more preferably 5 to 15 nm. When the average particle diameter (shell average particle diameter) of the cerium oxide particles is 2 nm or more, the selectivity of an oxygen-containing polar functional group in the compound having a hydrogenation reactive site and the oxygen-containing polar functional group is effectively improved, and, when the average particle diameter of the cerium oxide particles is 40 nm or less, the conversion of an oxygen-containing polar functional group in the compound having a hydrogenation reactive site and the oxygen-containing polar functional group is effectively improved.

When the silver-cerium oxide composite has a core-shell structure, there is no particular limitation with respect to the shape of the silver-cerium oxide composite, but the silver-cerium oxide composite is preferably an independent particle. Further, the shape of the particle may be substantially spherical. When the shape of the silver-cerium oxide composite particle is substantially spherical, the obtained actions and effects are presumed as follows.

Specifically, the reason why high selectivity to an oxygen atom in the oxygen-containing polar functional group is obtained by the silver-cerium oxide composite used in the selective hydrogenation catalyst of the invention is presumed that a hydrogen species having high polarity due to heterolytic cleavage of a hydrogen molecule is efficiently formed and almost no hydrogen species having low polarity due to homolytic cleavage of a hydrogen molecule is formed. The heterolytic cleavage of a hydrogen molecule occurs near the boundary surface between the silver particle and the cerium oxide, and the homolytic cleavage of a hydrogen molecule occurs on the surface of the silver particle.

It is presumed that when the silver-cerium oxide composite used in the invention is a silver-cerium oxide composite of a core-shell structure in which the surface of the silver particle in the composite is appropriately covered with cerium oxide, most of the active sites to which the substrate as a reactive molecule has access can be present near the boundary surface between the silver particle and the cerium oxide, and further there are less surfaces of only the silver particles on which homolytic cleavage of a hydrogen molecule is likely to occur.

(Shape of the Silver-Cerium Oxide Composite)

When the shape of the silver-cerium oxide composite used in the invention is substantially spherical, uniformly covering the silver particle with cerium oxide is facilitated, and the formation of a catalyst which is likely to achieve the above-mentioned actions is facilitated, and a catalyst having high selectivity may be obtained.

When the shape of the silver-cerium oxide composite used in the invention is a substantially spherical core-shell structure, the structure may be in a state in which the silver particle is completely covered with the cerium oxide, or in a state in which the silver particle is incompletely covered with the cerium oxide so that there are gaps between the adjacent cerium oxide particles. When part of the silver particle is exposed, there is no particular limitation with respect to the exposed state of the particle, but, when the silver particle is slightly exposed, excellent reactivity and excellent selectivity may be obtained with respect to an oxygen-containing polar functional group in the compound having a hydrogenation reactive site and the oxygen-containing polar functional group.

The covering state of the cerium oxide is also influenced by the above-mentioned metal silver (Ag)/cerium oxide ($CeO_2$) molar ratio. In a typical state, cerium oxide in a particle form covers the surface of the core formed from a silver particle, and the silver particle constituting the core is exposed through gaps between the adjacent cerium oxide particles.

(Alkaline Carrier)

With respect to the alkaline carrier which is a carrier (matrix material) for the catalyst of the invention, there is no particular limitation, and, for example, there can be mentioned a carrier containing at least one metal selected from alkali metals and alkaline earth metals. Specifically, there can be mentioned oxides, hydroxides, and carbonates containing at least one metal selected from alkali metals and alkaline earth metals, and, more specifically, there can be mentioned oxides, such as hydrotalcite, montmorillonite, magnesia, calcium oxide, and barium oxide; hydroxides, such as magnesium hydroxide and calcium hydroxide; and carbonates, such as calcium carbonate. The alkaline carrier may be solely an alkaline carrier, or a mixture of an alkaline carrier and a neutral carrier, such as alumina or silica, or may be a neutral carrier having carried thereon an alkali component. In the invention, of these, hydrotalcite, magnesia, or the like is preferred. As the alkaline carrier, preferred is one in which the counter-anion is not a strong acid and the alkali component is not dissolved in an aqueous solution. The reason for this is that the alkaline carrier in the invention is considered to serve not only as a carrier for dispersing the silver-cerium oxide composite which is a catalyst component but also as an oxidation-reduction reaction site for forming the silver-cerium oxide composite, and the base point present on the surface of the solid in a solution is considered to be advantageous.

With respect to the above-mentioned hydrotalcite, there is no particular limitation, and naturally produced hydrotalcite may be used, or synthetic hydrotalcite or a synthetic hydrotalcite-like compound may be used.

The hydrotalcite is represented by, for example, the following formula (1):

$$M^{II}{}_{8-X}M^{III}{}_{X}(OH)_{16}A \cdot nH_2O \qquad (1)$$

wherein $M^{II}$ represents at least one bivalent metal selected from $Mg^{2+}$, $Fe^{2+}$, $Zn^{2+}$, $Ca^{2+}$, $Li^{2+}$, $Ni^{2+}$, $Co^{2+}$, $Cu^{2+}$, and $Mn^{2+}$, $M^{III}$ represents at least one trivalent metal selected from $Al^{3+}$, $Fe^{2+}$, $Mn^{3+}$, and $Ru^{3+}$, x represents an integer of 1 to 7, A represents a bivalent anion, and n represents an integer of 0 to 30,
or the following formula (2):

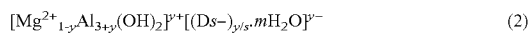
(2)

wherein y represents the number which satisfies the relationship: $0.20 \leq y \leq 0.33$, Ds− represents an s-valent anion, and m represents an integer of 0 to 30.

With respect to the hydrotalcite in the invention, especially from the viewpoint of obtaining an intended compound in an extremely high yield, preferred is hydrotalcite represented by the formula (1) above wherein $M^{II}$ is $Mg^{2+}$, $M^{III}$ is $Al^{3+}$, and A is $CO_3^{2-}$, and, particularly, hydrotalcite represented by $Mg_6Al_2(OH)_{16}CO_3 \cdot nH_2O$ can be preferably used.

Of these alkaline carriers, ones comprising at least magnesium oxide are preferred, and hydrotalcite ($Mg_6Al_2(CO_3)(OH)_{16} \cdot 4H_2O$), magnesia (MgO), and the like are especially preferred.

With respect to the various physical properties of the alkaline carrier, including adsorptivity, there is no particular limitation, and, for example, the adsorptivity of the alkaline carrier may be 0.1 to 300 $m^2/g$, in terms of a so-called BET value, and the average particle diameter of the alkaline carrier may be 0.1 to 100 μm. In the invention, the adsorptivity of the alkaline carrier is preferably 0.5 to 180 $m^2/g$.

Further, with respect to the form of the alkaline carrier, there is no particular limitation, and, for example, there can be mentioned a powdery form, a spherical particle form, an indefinite granular form, a cylindrical pellet form, an extruded form, and a ring form.

In the catalyst of the invention, with respect to the mode of the silver-cerium oxide composite supported on the alkaline carrier, there is no particular limitation, and various modes can be employed according to the form of the alkaline carrier, and the position of the carrier on which the oxide composite is supported may not be controlled, and may be inside of the pores or may be merely the surface of the carrier. Alternatively, a mode may be employed such that the silver-cerium oxide composite is supported on a carrier having an alkali component modified with a neutral carrier. In the catalyst of the invention, with respect to the amount of the silver-cerium oxide composite supported on the alkaline carrier, there is no particular limitation, and, for example, the amount is preferably 0.1 to 10 wt %, in terms of an amount of metal silver.

Since the catalyst of the invention naturally has a large particle diameter, as compared to the silver-cerium oxide composite, it is easy to separate after use in a reaction and, needless to say, is advantageous to reuse.
(Method for Producing the Catalyst of the Invention)

The catalyst of the invention can be produced by preparing a mixture containing at least a silver compound, a cerium compound, and an alkaline carrier and drying the mixture.

With respect to the silver compound used in the above-mentioned method, there is no particular limitation as long as the compound causes silver particles constituting the silver-cerium oxide composite when the mixture is prepared. As the silver compound, for example, there can be mentioned water-soluble salts, such as a nitrate, an acetate, a chloride, a sulfate, a sulfite, and an inorganic complex salt of silver, and, of these, a nitrate of silver is preferred.

With respect to the cerium compound used in the above-mentioned method, there is no particular limitation as long as the compound causes cerium oxide constituting the silver-cerium oxide composite when the mixture is prepared.

As the cerium compound, for example, there can be mentioned water-soluble salts, such as a nitrate, an acetate, a chloride, a sulfate, a sulfite, and an inorganic complex salt of cerium, and, of these, a nitrate of cerium is preferred.

With respect to the alkaline carrier used in the above-mentioned method, the same alkaline carrier as mentioned above can be used.

A mixture containing at least the above silver compound, cerium compound, and alkaline carrier can be obtained by, for example, adding a silver compound, a cerium compound, and an alkaline carrier to a solvent, such as water, and heating the resultant mixture to about 50 to 100° C. and maintaining that temperature for about 1 to 48 hours. With respect to the amounts of the silver compound, cerium compound, and alkaline carrier added, there is no particular limitation, and, for example, relative to 0.1 mmol of metal silver, the amount of the alkaline carrier is 0.1 to 10 g, preferably 1 to 3 g, and the cerium compound may be added so as to satisfy the above-mentioned compositional ratio of silver to cerium oxide.

With respect to the order of adding the silver compound, the cerium compound, and the alkaline carrier to a solvent, there is no particular limitation, and, for example, it is preferred that the silver compound and the cerium compound are added to a solvent and then the alkaline carrier is added to the resultant mixture. Methanol, ethanol, acetone, or the like can be further added to the solvent.

The mixture is prepared as mentioned above and then, the mixture is dried to obtain the catalyst of the invention. The temperature for drying is not particularly limited, and, for example, may be room temperature of about 5 to 35° C. Before drying, a separation method, such as filtration or centrifugal separation, or a washing method may be performed.

In the method for producing the catalyst of the invention, the mechanism causing the silver compound and the cerium compound to constitute a core-shell form on the alkaline carrier is presumed that an oxidation-reduction reaction of silver (I)-cerium (III) to silver (0)-cerium (IV) occurs at the base point of the alkaline carrier, and metal silver, which is likely to suffer aggregation, first forms a core of silver and then cerium oxide is deposited around the core.
(Selective Hydrogenation)

The catalyst of the invention obtained as mentioned above can be used in selective hydrogenation (selective reduction reaction) like a conventional silver-cerium oxide composite. The catalyst of the invention can be used in a material for an exhaust gas treatment catalyst for automobile or the like, or a hydrogen sensor, and the like, and is preferably used in selective hydrogenation of an organic compound, more preferably used in selective hydrogenation of an oxygen-containing polar functional group in an organic compound having an oxygen-containing polar functional group which is any one of a nitro group, an aldehyde group, and an epoxy group and having a hydrogenation reactive site. As examples of the hydrogenation reactive sites, there can be mentioned a carbon-carbon double bond, an aromatic ring, and a heterocycle.

With respect to the above-mentioned organic compound having an oxygen-containing polar functional group which is any one of a nitro group, an aldehyde group, and an epoxy group and having a hydrogenation reactive site, there is no particular limitation, and, for example, there can be mentioned those described in the International Publication No. WO2014/119766 pamphlet, e.g., terpenoids, such as nitrostyrene, nitrostyrylbenzene, and citral, and epoxy compounds, such as stilbene oxide, styrene oxide, methyl styrene oxide, fluorostyrene oxide, chlorostyrene oxide, and ethyl epoxycinnamate.

With respect to the method for selectively hydrogenating an organic compound using the catalyst of the invention, there is no particular limitation, and the method may be appropriately selected according to the type of the organic compound to be hydrogenated and the hydrogenation of the organic compound.

For example, with respect to an organic compound having an oxygen-containing polar functional group which is anyone of a nitro group, an aldehyde group, and an epoxy group and having a hydrogenation reactive site, when selectively hydrogenating the oxygen-containing polar functional group in the organic compound using the catalyst of the invention, the selective hydrogenation is performed by bringing the catalyst of the invention, the organic compound, and hydrogen gas into contact with one another in a solvent. A reaction mechanism of the selective hydrogenation in the invention is presumed that a hydrogen molecule heterolytically dissociates between silver and cerium oxide, and the resultant has no ability to hydrogenate a carbon-carbon double bond but has the ability to hydrogenate a polarized functional group, such as epoxy, nitro, or aldehyde, to achieve selective hydrogenation.

With respect to the solvent used in the hydrogenation, there is no particular limitation, and, for example, at least one organic solvent selected from aliphatic hydrocarbons having 5 to 20 carbon atoms, such as dodecane and cyclohexane; aromatic hydrocarbons having 7 to 9 carbon atoms, such as toluene and xylene; ethers having a chain structure or a cyclic structure, such as oxetane, tetrahydrofuran (THF), tetrahydropyran (THP), furan, and dibenzofuran; and polyethers, such as polyethylene glycol and polypropylene glycol, or a mixture of water and an organic solvent is preferred, and, particularly, only an organic solvent is preferably used. Of these solvents, toluene is especially preferred because it has high stability to hydrogenation.

The hydrogenation is conducted in the presence of a solvent, and, with respect to the amount of the solvent, the solvent is preferably used in such an amount that, for example, the concentration of the above-mentioned organic compound becomes about 0.5 to 2.0% by mass. The amount of the catalyst of the invention used in the hydrogenation is, for example, about 0.0001 to 50 mol %, preferably about 0.01 to 20 mol %, more preferably about 0.1 to 5 mol %, based on the mole of the organic compound. In this hydrogenation, the reaction can be smoothly proceed even under mild conditions. The reaction temperature can be appropriately controlled according to the type of the substrate, the type of the intended product, or the like, and is, for example, 10 to 100° C., preferably about 10 to 50° C., especially preferably about 10 to 40° C. The reaction time can be appropriately controlled according to the reaction temperature and pressure, and is, for example, about 10 minutes to 48 hours, preferably about 1 to 48 hours, especially preferably about 4 to 30 hours.

With respect to the above-mentioned selective hydrogenation, when the organic compound is, for example, an epoxy compound represented by the formula (1) below described in JP-A-2011-236165, oygen in an epoxy group of the epoxy compound is selectively hydrogenated and dehydrated, that is, so-called deoxygenation of the epoxy compound is performed to form an alkene compound represented by the formula (2) below.

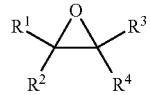

(1)

wherein $R^1$, $R^2$, $R^3$, and $R^4$ are the same or different and each represents a hydrogen atom or a hydrocarbon group, and two substituents selected from $R^1$, $R^2$, $R^3$, and $R^4$ are optionally bonded and form a ring together with the carbon atom forming the epoxy ring, with the proviso that at least one of $R^1$, $R^2$, $R^3$, and $R^4$ is a hydrocarbon group.

In the above formula, examples of the hydrocarbon groups for $R^1$, $R^2$, $R^3$, and $R^4$ include aliphatic hydrocarbon groups, alicyclic hydrocarbon groups, aromatic hydrocarbon groups, and groups formed from the above hydrocarbon groups bonded to each other. The above hydrocarbon groups include hydrocarbon groups having a substituent. Examples of aliphatic hydrocarbon groups include alkyl groups having about 1 to 4 (preferably 1 to 3) carbon atoms, such as a methyl group, an ethyl group, a propyl group, an isopropyl group, and a butyl group. Examples of alicyclic hydrocarbon groups include about 3- to 12-membered (preferably 3- to 8-membered, especially preferably 5- to 8-membered) cycloalkyl groups, such as a cyclopropyl group, a cyclobutyl group, a cyclopentyl group, a cyclohexyl group, a cycloheptyl group, and a cyclooctyl group; and about 3- to 8-membered (preferably 5- to 8-membered) cycloalkenyl groups, such as a cyclopentenyl group. Examples of aromatic hydrocarbon groups include aromatic hydrocarbon groups having about 6 to 14 (preferably 6 to 10) carbon atoms, such as a phenyl group. Examples of hydrocarbon groups formed from an aliphatic hydrocarbon group and an alicyclic hydrocarbon group which are bonded to each other include cycloalkyl-alkyl groups (for example, $C_3$-$C_{12}$ cycloalkyl-$C_1$-$C_4$ alkyl groups), such as a cyclopentylmethyl group, a cyclohexylmethyl group, and a 2-cyclohexylethyl group. Examples of hydrocarbon groups formed from an aliphatic hydrocarbon group and an aromatic hydrocarbon group which are bonded to each other include aralkyl groups (for example, aralkyl groups having 7 to 18 carbon atoms) and alkyl-substituted aryl groups (for example, a phenyl group substituted with about 1 to 4 alkyl groups having 1 to 4 carbon atoms). The hydrocarbon group may have various substituents, for example, a halogen atom, an oxo group, a hydroxyl group, or a substituted oxy group (for example, an alkoxy group, an aryloxy group, or an aralkyloxy group). The hydroxyl group may be protected by a protecting group commonly used in the field of organic synthesis. As a specific example of the epoxy compound preferaly used, there can be mentioned stilbene oxide.

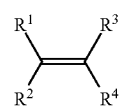

(2)

wherein $R^1$, $R^2$, $R^3$, and $R^4$ are as defined above.

Like the above-mentioned hydrogenation, the deoxygenation can be performed by bringing the catalyst of the invention, the organic compound, and hydrogen gas into contact with one another in a solvent, and the conditions for the deoxygenation may be the same as those for the hydrogenation.

After completion of the above-mentioned selective hydrogenation, the hydrogenated compound can be separated and purified by, for example, a separation method, such as filtration, concentration, distillation, extraction, crystal deposition, recrystallization, or column chromatography, or a combination of these separation methods.

(Reuse of the Catalyst)

The catalyst of the invention is supported on the alkaline carrier, and therefore, when used in the selective hydrogenation, the supported silver is unlikely to be dissolved in the reaction solution during the reaction, and, after the hydrogenation, the catalyst can be easily recovered from the reaction solution, for example, by a physical separation method, such as filtration or centrifugal separation. The recovered silver-cerium oxide supported composite catalyst is reused as such, or is subjected to washing and drying treatments and then reused. The washing treatment can be conducted by a method of washing the recovered catalyst with an appropriate solvent (for example, water) several times (for example, two or three times).

The recovered catalyst of the invention can exhibit catalysis almost equivalent to that of an unused silver-cerium oxide supported composite catalyst and hence, even when a cycle of the operations of using and recovering the catalyst is repeated multiple times, for example, about 5 times, a lowering of the catalysis can be remarkably suppressed. Therefore, in the invention, the silver-cerium oxide supported composite catalyst, which generally accounts for a large proportion of the cost of hydrogenation, can be recovered and repeatedly used, thereby making it possible to markedly reduce the cost of hydrogenation of an organic compound.

EXAMPLES

Hereinbelow, the silver-cerium oxide supported composite catalyst (AgNPs@CeO$_2$-D) of the invention and the Examples of the invention will be described in more detail, but the following Examples should not be construed as limiting the scope of the invention, and the invention is widely applicable within the scope of the invention.

Production Example 1

Production of a Catalyst A 0.1 mmol of silver nitrate (AgNO$_3$) and 0.1 mmol of cerium nitrate (Ce(NO$_3$)$_3$) were added to 50 mL of water, and then 2.0 g of hydrotalcite (HT) was added thereto and the resultant mixture was stirred at 90° C. for 2 hours.

The resultant mixture having a black precipitate formed was subjected to filtration, and the collected material was washed with pure water and then dried at room temperature to obtain a precipitate.

Figure 3:
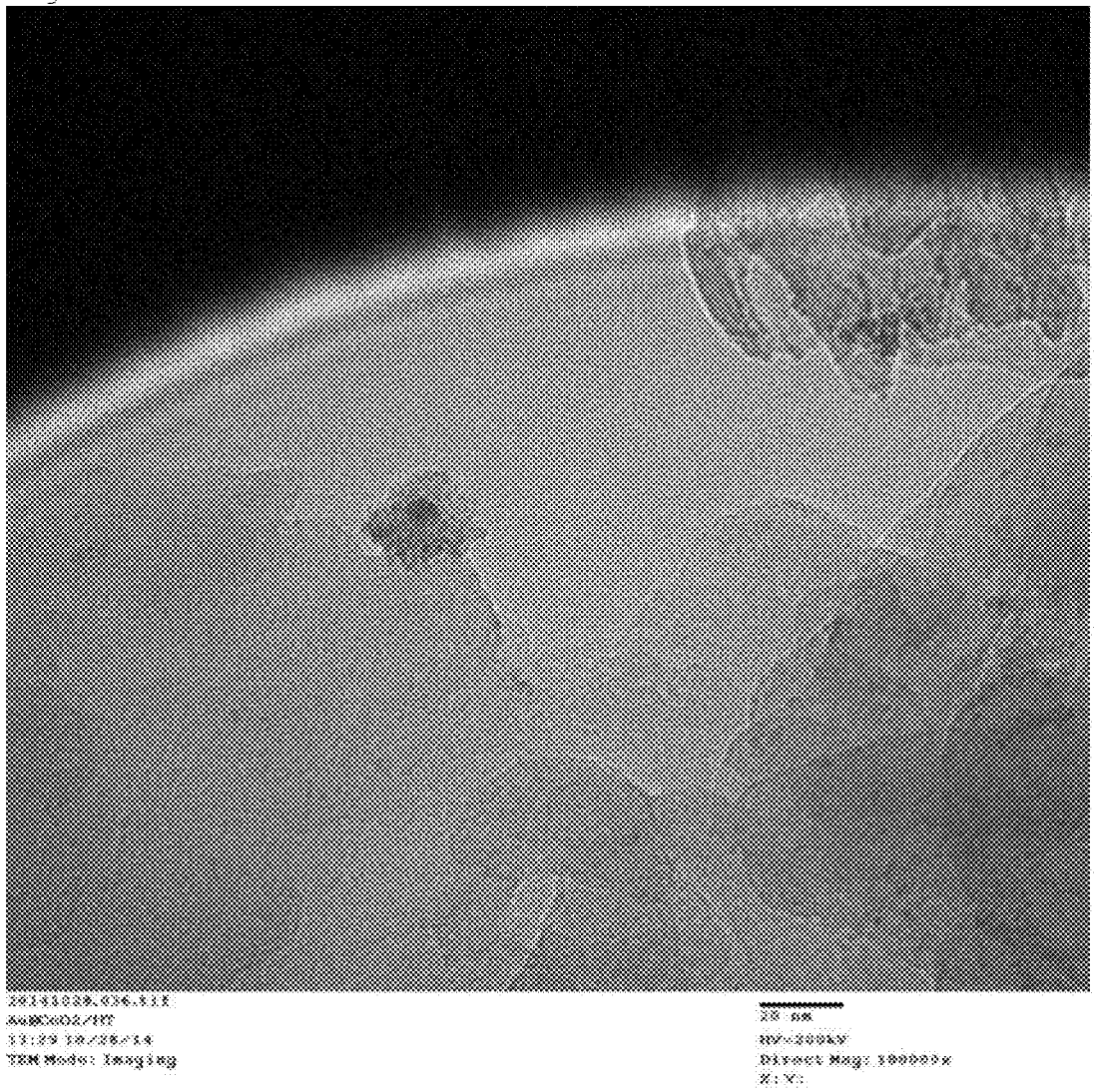
FIG. 3 is a TEM image of the silver-cerium oxide composite catalyst obtained in Production Example 1 (magnification: 100,000 times).

The thus obtained precipitate was examined by means of a TEM. As a result, it was found that a silver-cerium oxide composite was supported on hydrotalcite, wherein the silver-cerium oxide composite had a core-shell structure which has a silver nano-particle having a particle diameter of about 10 nm as a core and cerium oxide covering the core, and the result confirmed that the catalyst (AgNPs@CeO$_2$—HT) of the invention was produced. A TEM image of the produced AgNPs@CeO$_2$—HT is shown in FIG. 3. The scale in the TEM image indicates 20 nm.

Production Example 2

Production of a Catalyst B

A precipitate was obtained in substantially the same manner as in Production Example 1 except that magnesia (MgO) was used in place of hydrotalcite. The color of the precipitate in the mixture after being stirred was found to have changed to black.

Figure 4:
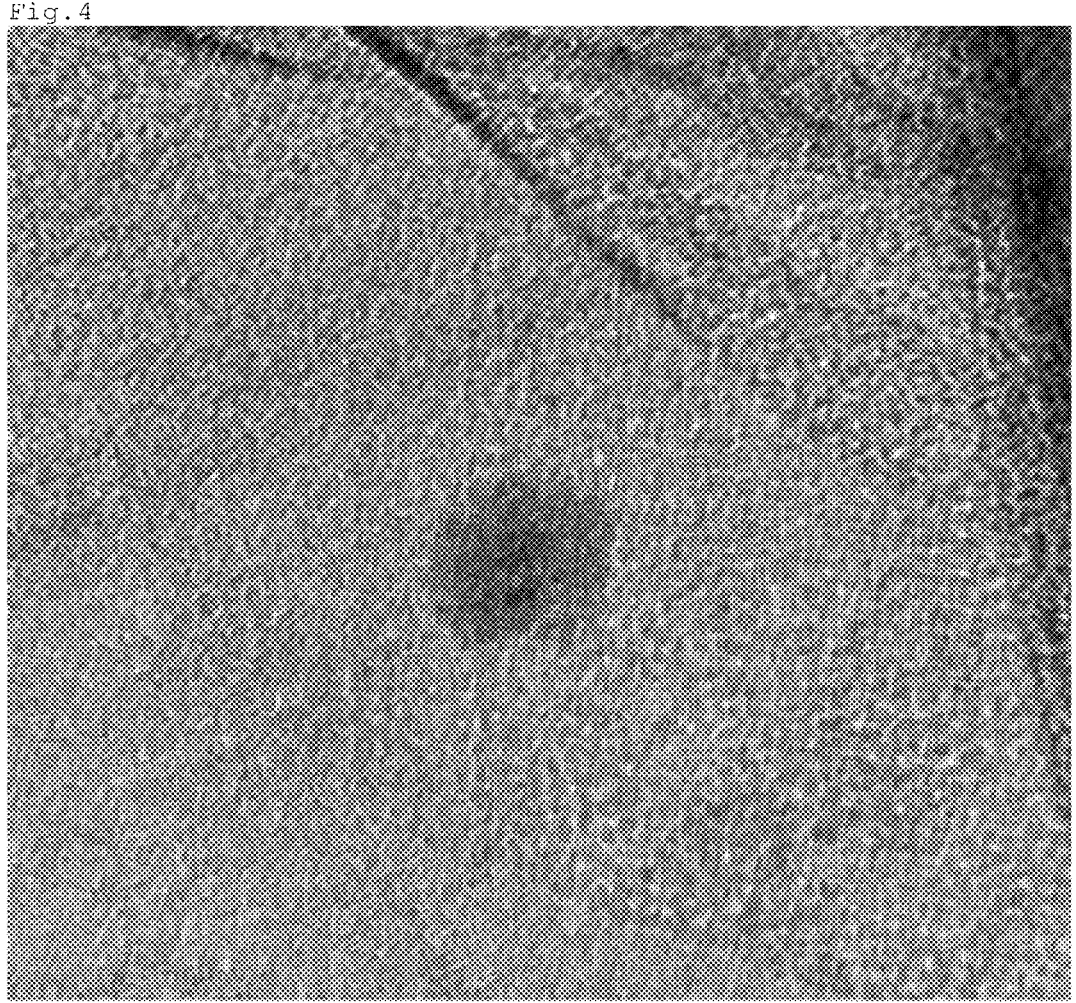
FIG. 4 is a TEM image of the silver-cerium oxide composite catalyst obtained in Production Example 2 (magnification: 300,000 times).

The thus obtained precipitate was examined by means of a TEM. As a result, it was found that a silver-cerium oxide composite was supported on magnesia, wherein the silver-cerium oxide composite had a core-shell structure which has a silver nano-particle having a particle diameter of about 5 nm as a core and cerium oxide covering the core, and the result confirmed that the catalyst (AgNPs@CeO$_2$—MgO) of the invention was produced. A TEM image of the produced AgNPs@CeO$_2$—MgO is shown in FIG. 4. The scale in the TEM image indicates 5 nm.

Production Example 3

Production of a Catalyst C

A precipitate was obtained in substantially the same manner as in Production Example 1 except that calcium carbonate (CaCO$_3$) was used in place of hydrotalcite. The color of the precipitate in the mixture after being stirred was found to have changed to black.

Example 1

Selective Changing of Epoxy Group to Alkene

A reduction treatment was conducted for 20 hours under conditions such that the amount of the catalyst A (AgNPs@CeO$_2$—HT) obtained in Production Example 1 was 1 mol % or the amount of the catalyst B (AgNPs@CeO$_2$—MgO) obtained in Production Example 2 was 4 mol %, the amount of stilbene oxide as a substrate was 0.5 mmol, the amount of toluene as a solvent was 5 mL, the hydrogen pressure was 6 atm, and the reaction temperature was 110° C. After the reduction treatment, a yield and a selectivity were measured using gas chromatography. The results are shown in Table 1.

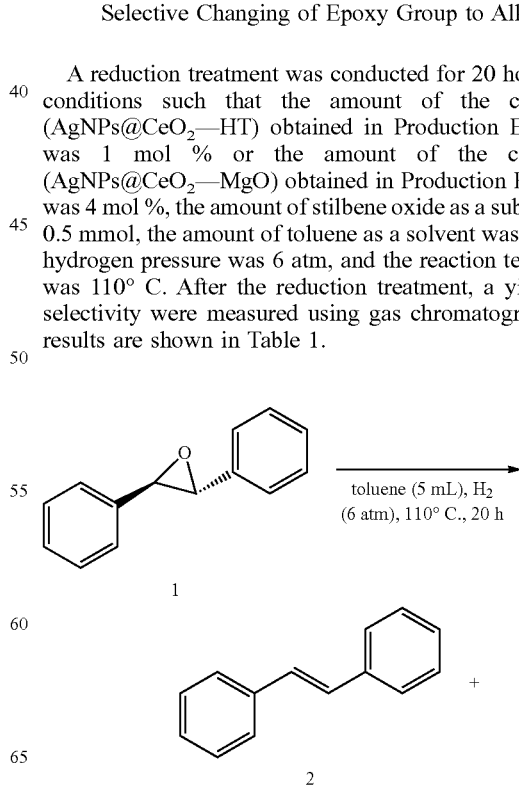

-continued

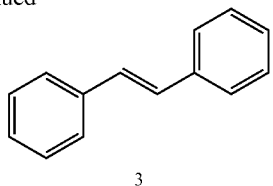

3

TABLE 1

| Catalyst | Conversion (%) | Yield of 2 (%) | Selectivity (%) | Catalyst amount |
|---|---|---|---|---|
| Catalyst A | 99 | 99 | 100 | 1 mol % |
| Catalyst B | 84 | 84 | 100 | 4 mol % |

When the catalyst A using hydrotalcite as a carrier was used, the yield was 99% and the selectivity was 100%. Further, when the catalyst B using magnesia as a carrier was used, the yield was 84% and the selectivity was 100%. From the above, it has been found that both the catalyst A and catalyst B exhibit excellent catalysis in the deoxygenation reaction of stilbene oxide.

Example 2

Selective Hydrogenation of an Aldehyde Group

A reduction treatment was conducted for 4 hours under conditions such that the amount of the catalyst A (AgNPs@CeO$_2$—HT) obtained in Production Example 1 or the catalyst C (AgNPs@CeO$_2$—CaCO$_3$) obtained in Production Example 3 was 6 g, the amount of cinnamaldehyde as a substrate was 7.5 mmol, the amount of THF as a solvent was 50 mL, the hydrogen pressure was 6 atm, and the reaction temperature was 110° C. After the reduction treatment, a yield and a selectivity were measured using gas chromatography. The results are shown in Table 2.

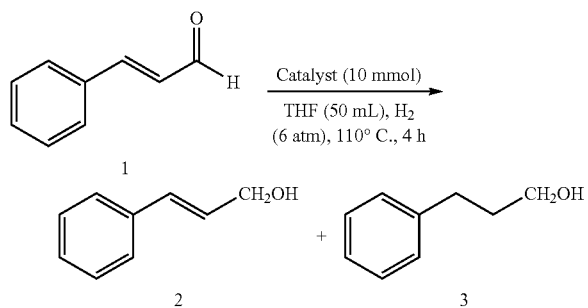

TABLE 2

| Catalyst | Conversion (%) | Yield of 2 (%) | Selectivity (%) |
|---|---|---|---|
| Catalyst A | 29.3 | 28.2 | 96 |
| Catalyst C | 23.4 | 22.9 | 98 |

When the catalyst A using hydrotalcite as a carrier was used, the yield was 29.3% and the selectivity was 96%. Further, when the catalyst C using calcium carbonate as a carrier was used, the yield was 23.4% and the selectivity was 98%. From the above, it has been found that both the catalyst A and catalyst C exhibit excellent catalysis in the selective hydrogenation reaction of an aldehyde group of cinnamaldehyde to an alcohol.

Comparative Production Example 1

Production of a Catalyst D

A precipitate was obtained in substantially the same manner as in Production Example 1 except that hydroxyapatite (HAP) was used in place of hydrotalcite. The color of the precipitate in the mixture after being stirred was found to remain white.

The thus obtained precipitate was examined by means of an XPS. As a result, a peak for silver was observed, which confirmed that a core-shell type catalyst was not produced.

Comparative Production Example 2

Production of a Catalyst E

A precipitate was obtained in substantially the same manner as in Production Example 1 except that silica-alumina (SiO$_2$.Al$_2$O$_3$) was used in place of hydrotalcite. The color of the precipitate in the mixture after being stirred was found to remain white.

The thus obtained precipitate was examined by means of an XPS. As a result, a peak for silver was observed, which confirmed that a core-shell type catalyst was not produced.

Comparative Production Example 3

Production of a Catalyst F

A precipitate was obtained in substantially the same manner as in Production Example 1 except that cerium oxide (CeO$_2$) was used in place of hydrotalcite. The color of the precipitate in the mixture after being stirred was found to remain white. This shows that a core-shell type catalyst was not produced.

From the above results, it is apparent that, by using an alkaline carrier, the catalyst of the invention comprising a silver-cerium oxide composite supported on the alkaline carrier can be easily produced.

Further, it is apparent that, merely by checking whether the color of the precipitate in the mixture after being stirred is changed or not, it is possible to know whether the catalyst of the invention has been produced, and the judgement can be easily made.

INDUSTRIAL APPLICABILITY

The catalyst of the invention is advantageously used in a deoxygenation reaction of an aromatic compound having an epoxy group, which is useful as an intermediate in various medicines and agricultural chemicals and in other various industrial fields, the production of a terpenoid containing a carbon-carbon double bond and a hydroxyl group, and a functional material for a catalyst for automobile, a sensor, and the like utilizing the specific hydrogenation reaction properties. Further, the catalyst of the invention can be inexpensively and safely produced.

What is claimed is:

1. A silver-cerium oxide supported composite catalyst comprising:
    a silver-cerium oxide composite and
    an alkaline carrier having supported thereon the oxide composite,
    wherein the silver-cerium oxide composite comprises a silver particle and cerium oxide covering the surface of the silver particle.

2. The silver-cerium oxide supported composite catalyst according to claim 1, wherein the alkaline carrier comprises at least one metal selected from the group consisting of alkali metals and alkaline earth metals.

3. The silver-cerium oxide supported composite catalyst according to claim 1, wherein the alkaline carrier comprises at least magnesium oxide.

4. The silver-cerium oxide supported composite catalyst according to claim 1, wherein the silver-cerium oxide composite has a [metal silver (Ag)/cerium oxide ($CeO_2$)] molar ratio of 0.25 to 4.0, wherein the [metal silver (Ag)/cerium oxide ($CeO_2$)] molar ratio is a ratio of the mole of silver in terms of metal silver in the silver particle to the mole of the cerium oxide.

5. The silver-cerium oxide supported composite catalyst according to claim 1, wherein the silver-cerium oxide composite has a core-shell structure.

6. The silver-cerium oxide supported composite catalyst according to claim 1, wherein the alkaline carrier comprises hydrotalcite or magnesia.

7. The silver-cerium oxide supported composite catalyst according to claim 1, in a form suitable for use in selective hydrogenation.

8. The silver-cerium oxide supported composite catalyst according to claim 7, wherein the selective hydrogenation is hydrogenation of an oxygen-containing polar functional group which is any one of a nitro group, an aldehyde group, or an epoxy group.

9. A selective hydrogenation method for an organic compound, comprising selectively hydrogenating an organic compound using the silver-cerium oxide supported composite catalyst according to claim 1.

10. The selective hydrogenation method according to claim 9, wherein the organic compound is a compound having an oxygen-containing polar functional group which is any one of a nitro group, an aldehyde group, or an epoxy group and having a hydrogenation reactive site, wherein the oxygen-containing polar functional group of the compound is selectively hydrogenated.

11. A method for producing a silver-cerium oxide supported composite catalyst which comprises a silver-cerium oxide composite and an alkaline carrier having supported thereon the oxide composite, the silver-cerium oxide composite comprising a silver particle and cerium oxide covering the surface of the silver particle,
    the method comprising preparing a mixture containing at least a silver compound, a cerium compound, and an alkaline carrier, and drying the mixture.

12. The method according to claim 11, wherein the alkaline carrier comprises at least magnesium oxide.

13. The method according to claim 11, wherein the alkaline carrier comprises hydrotalcite or magnesia.

14. The method according to claim 11, wherein the mixture containing at least a silver compound, a cerium compound, and an alkaline carrier is prepared by mixing together the silver compound and the cerium compound, and then adding the alkaline carrier to the resultant mixture.

* * * * *